United States Patent [19]

Rouse, 3 et al.

[11] Patent Number: 5,496,861
[45] Date of Patent: Mar. 5, 1996

[54] COSMETICS CONTAINING ENZYMATICALLY DEBRANCHED STARCH

[75] Inventors: William Rouse, 3, Lakewood, Ohio; Maria Valles, Colonia, N.J.; Gary T. Martino, Plainsboro, N.J.; Chung-Wai Chiu, Westfield, N.J.

[73] Assignee: National Starch and Chemical Investment Holding Corporation, Wilmington, Del.

[21] Appl. No.: 186,408

[22] Filed: Jan. 24, 1994

Related U.S. Application Data

[63] Continuation of Ser. No. 615,725, Nov. 19, 1990, abandoned.

[51] Int. Cl.$^6$ ............. A61K 7/42; A61K 7/48; A61K 9/10; A61K 9/107
[52] U.S. Cl. ............. 514/778; 252/315.3; 424/DIG. 5; 424/59; 424/60; 424/63; 424/65; 514/777; 514/781; 514/938; 514/847; 512/4; 512/5
[58] Field of Search ............. 514/844, 847, 514/777, 781, 778

[56] References Cited

U.S. PATENT DOCUMENTS

| | | | |
|---|---|---|---|
| 3,729,380 | 4/1973 | Sugimoto et al. | 195/31 R |
| 3,957,969 | 5/1976 | Fujiyama et al. | 424/64 |
| 4,221,609 | 9/1980 | Hughes | 127/29 |
| 4,913,743 | 4/1990 | Brode et al. | 106/162 |
| 4,927,636 | 5/1990 | Hijiya et al. | 514/777 |
| 4,970,220 | 11/1990 | Chaussee | 514/358 |
| 4,971,828 | 11/1990 | Abbas et al. | 426/661 |
| 4,981,709 | 1/1991 | Furcsik et al. | 426/565 |
| 5,051,271 | 9/1991 | Iyengar et al. | 426/658 |
| 5,089,171 | 2/1992 | Chiu | 252/315.3 |

FOREIGN PATENT DOCUMENTS

| | | | |
|---|---|---|---|
| 53/127841 | 11/1978 | Japan | A61K 7/02 |
| 53/12784 | 11/1978 | Japan | A61K 7/02 |
| 89/09793 | 10/1989 | WIPO | C08B 30/12 |
| 87/12403 | 12/1989 | WIPO | A23L 1/10 |

OTHER PUBLICATIONS

Anon., *Bulletin—Leatherhead Food R.A.*, vol. 22, No. 6, Jun. 1988.
Braudo, Von E. E., et al., "Struktur und Eigenschaften von Maltodextrin–Hyrogelen," Starch/Starke 31:188–194 (1979). (Translation to English Provided).
Anon., *Annual Review 1989 Leatherhead Food R.A.*, p. 24.

Primary Examiner—Dale R. Ore
Attorney, Agent, or Firm—Ellen T. Dec

[57] ABSTRACT

Emulsion-containing cosmetic compositions, wherein the emulsion comprises an aqueous dispersion of 15 to 40% solids, by weight, of an enzymatically degraded starch, which starch has been debranched by treatment with an alpha-1,6-D-glucanohydrolase to yield up to 100%, by weight, short chain amylose, are provided herein. Also provided are oil-free cosmetic compositions and cosmetic stick compositions, comprising 1 to 16% enzymatically debranched starch; 2 to 35% water; 35 to 90% hydrophobic base, selected from the group consisting of oil, wax and fat, and 5 to 20% emulsifier(s), with the balance of the compositions comprising one or more adjuncts selected from dye(s), fragrance(s), flavor(s), sunscreen agent(s), opacifier(s), and filler(s). Also provided is a method for formulating a cosmetic stick composition.

12 Claims, No Drawings

COSMETICS CONTAINING ENZYMATICALLY DEBRANCHED STARCH

This application is a continuation of application Ser. No. 07/615,725, filed Nov. 19, 1990 now abandoned.

This invention relates to cosmetics comprising enzymatically debranched starch, and in particular, cosmetics which are stable, smooth-textured, water-in-oil emulsions. This is a continuation-in-part of U.S. Pat. No. 4,971,723, issued Nov. 20, 1990, to Chiu.

BACKGROUND OF THE INVENTION

Humectant and tactile properties such as a soft feel on the skin and lips, and a smooth, easily spreadable texture are highly desirable in cosmetics. In stick products, such as lipstick, lip balm, stick deodorants and other similar cosmetics, a formulation providing a stable, rigid form, in addition to humectant and tactile properties, is highly desirable. These tactile properties are provided in conventional cosmetic compositions by hydrophobic ingredients such as waxes, oils and fats.

Improved humectant properties are provided by adding hydrophilic ingredients to the composition and forming a stable water-in-oil emulsion. The emulsion compositions known in the art suffer from several drawbacks including lack of emulsion stability, particularly in stick compositions and high ingredient costs (e.g., haluronic acid costs), particularly in cream, lotion and beauty soap compositions.

It has been discovered that cosmetic compositions containing certain enzymatically debranched starches are characterized by stability and excellent humectant and tactile properties. It has been discovered that oil-free lotions may be formulated with the enzymatically debranched starches. The enzymatically debranched starches have been characterized as having unique gelling, lubricating and film-forming properties in aqueous dispersion (U.S. Pat. No. 4,971,723, issued Nov. 20, 1990, to Chiu; and U.S. Pat. Nos. 4,886,678 to Chiu, et al., issued Dec. 12, 1989; and 4,937,091 to Zallie, et al., issued Jun. 26, 1990). U.S. Pat. No. 3,957,969 to Fujiyama, et al., issued May 18, 1976, discloses the use of various polyhydroxyl compounds, including starch, in cosmetic stick formulations. It now has been discovered that only enzymatically debranched starches, and not starches in general, are useful in cosmetic stick formulations.

Starch is a polysaccharide typically comprising a mixture of about 20–25% amylose and about 75–80% amylopectin which is organized into compact granular structures. Amylose is a linear polymer of D-anhydroglucose units which are linked by alpha-1,4-D-glucosidic bonds. Amylopectin is a large branched polymer of amylose chains linked by alpha-1,6-D-glucosidic bonds in a tree-like structure. Depending upon the variety of plant from which the starch is obtained, amylose ordinarily contains between 250 and 12,500 D-anhydroglucose units and amylopectin contains between 400,000 and 3,125,000 D-anhydroglucose units. As used herein, "short chain amylose" refers to linear polymers containing from about 15 to 65 anhydroglucose units linked by alpha-1,4-D-glucosidic bonds.

Enzymes, or mixtures of enzymes which saccharify and debranch starch, have been used in starch conversion processes for the commercial production of low molecular weight oligosaccharides and sugars, such as dextrose (glucose). Starch conversion is the degradation of starch to lower molecular weight components by treatment with acid, oxidizing agents, heat, alkali or alpha-amylase enzymes. Enzymatic conversion of starch typically involves preferential hydrolysis of the alpha-1,4-D-glucosidic bonds, and only limited, if any, hydrolysis of the alpha-1,6-D-glucosidic bonds.

Glucoamylase rapidly hydrolyzes alpha-1,4-D-glucosidic bonds and slowly hydrolyzes alpha-1,6-D-glucosidic bonds, releasing glucose. In contrast, a debranching enzyme, such as pullulanase or isoamylase, rapidly hydrolyzes only the alpha-1,6-D-glucosidic bonds, releasing short chain amylose.

Debranching enzymes (enzymes which release short chain amylose from starch) have been proposed for use in conjunction with glucoamylase and alpha-amylase to improve the efficiency of production of high dextrose syrups; in low calorie alcoholic beverage production to improve fermentability of branched starch fragments; in production of maltose from starch in conjunction with beta-amylase; in low DE maltodextrin (30–55 glucose units) production to induce proteins to aggregate in aqueous emulsions; and in enzymatic conversion of starch into a soluble syrup having a high quantity of disaccharides and trisaccharides. These debranching enzyme applications are directed to problems arising from the presence of branched starch or dextrin fragments following starch conversion processes. In each application, the debranching enzyme is employed in the complete conversion of starch to a variety of low molecular weight fragments such as sugars or maltodextrins. The thickening, adhesion and gelling characteristics of starch are lost.

The use of debranching enzymes to fully debranch starch, with hydrolysis of substantially all alpha-1,6-D-glucosidic bonds, so as to obtain pure, or amylopectin-free, low molecular weight amylose is taught in U.S. Pat. No. 3,730,840 to Sugimoto, et al.; U.S. Pat. No. 3,881,991 to Kurimoto, et al.; and U.S. Pat. No. 3,879,212 to Yoshida. The object of these patents is to produce pure short chain amylose. The presence of any residual amylopectin is taught to be objectionable. No disclosure is made of any lubricating or humectant properties or utilities within the field of cosmetics formulation.

Thus, the background of enzyme-related starch technology does not suggest that starches useful as ingredients in cosmetic compositions may be prepared by employing debranching enzymes to debranch the amylopectin component of starch, yielding short chain amylose, and, optionally, partially debranched amylopectin, native amylose, or amylopectin, with or without substantial conversion of the starch. These starches and the enzymatic process offer significant advantages over other products and processes in cosmetics where "natural" and "hypoallergenic" claims frequently appear in product marketing programs.

SUMMARY OF THE INVENTION

This invention provides enzymatically debranched starches, comprising 15 to 100%, by weight, short chain amylose, for use in cosmetics. Aqueous dispersions of these debranched starches are characterized by a variety of fat-like textures ranging from oily to creamy to waxy which are useful in cosmetics. These starches may be selected to provide high strength starch gels or thermoreversible starch gels in aqueous dispersions. A thermally reversible starch gel is one which melts upon heating and reforms upon cooling. Gels prepared from unmodified starches are not thermally reversible.

This invention also provides water-in-oil emulsion and oil-free cosmetic compositions, and cosmetic stick compositions, formulated with enzymatically debranched starches.

Emulsion-containing cosmetic compositions, wherein the emulsion comprises a 15 to 40% solids, by weight, aqueous dispersion of an enzymatically degraded starch, which starch has been debranched by treatment with an alpha-1,6-D-glucanohydrolase to yield up to 100%, by weight, short chain amylose, are provided herein.

Also provided are cosmetic stick compositions, comprising 1 to 16% starch which has been enzymatically debranched to yield from 15 to 100%, by weight, short chain amylose; 2 to 35% water; 35 to 90% hydrophobic base, selected from the group consisting of oil, wax and fat; and 5 to 20% emulsifier(s), with the balance of the compositions comprising one or more adjuncts selected from dye(s), preservative(s), fragrance(s), flavor(s), sunscreen agent(s), opacifier(s), and filler(s).

Also provided is a method for formulating a cosmetic stick composition which comprises:

a) dispersing an enzymatically debranched starch in an aqueous solvent at 15 to 40%, by weight, solids;

b) heating the dispersed starch to 70°–100° C.;

c) adding to the dispersed starch a hydrophobic phase at 70°–100° C., which hydrophobic phase comprises at least one hydrophobic ingredient and at least one emulsifier;

d) blending the dispersed starch into the hydrophobic phase to provide an emulsion; and e) forming the cosmetic stick from the emulsion; whereby the emulsion is uniform and the cosmetic stick composition is stable.

DESCRIPTION OF THE PREFERRED EMBODIMENTS

The starches which are enzymatically debranched for use herein may be derived from any source, including corn, potato, sweet potato, wheat, rice, sago, tapioca, waxy maize, sorghum, and the like. Also included are the conversion products derived from any of the above starches, including fluidity or thin-boiling starches prepared by oxidation, alpha-amylase conversion, mild acid hydrolysis or heat dextrinization. Crosslinked or derivatized starches, such as ethers and esters, and other modified starches also may be employed.

The starch will preferably be a gelatinized starch (a precooked, cold-water-swelling starch) and also may be a fluidity starch converted by mild acid degradation, heat dextrinization, or any one of several methods that are well known in the art. See, e.g., M. W. Rutenberg, "Starch and Its Modifications" P. 22–36, in *Handbook of Water-Soluble Gums and Resins*, R. L. Davidson, editor, McGraw Hill, Inc., New York, N.Y., 1980. If desired, the starch may be converted by treatment with an alpha-amylase to produce a fluidity starch in the manner disclosed in U.S. Pat. No. 4,726,957 to Lacourse, et al. A combination of one or more of these conversion techniques may be used. The conversion is typically carried out before derivatization or crosslinking, but may be carried out before or after the enzymatic treatment. Where a high viscosity debranched starch is desired, it is not desirable to convert the starch.

Where a low viscosity starch is desirable, a starch, such as waxy maize, which has been converted to a Water Fluidity (WF) of up to about 60 is preferred. Water Fluidity is an empirical measure of viscosity on a scale of 0–90, wherein fluidity is the reciprocal of viscosity.

For other products, derivatization to any degree of substitution or level of conversion that results in the desired viscosity and functional characteristics may be employed prior to, or following, enzymatic debranching. For example, the debranched starch may be employed as an emulsifying agent in cosmetics (e.g., the moisturizer sunscreen formulation herein) and an emulsifying starch, such as octenylsuccinate derivative (OSA starch), is preferred. The starch is treated with octenylsuccinic acid anhydride to form a starch ester derivative containing from 0.25 to 3.0%, by weight, of octenylsuccinate.

In a preferred embodiment, the next step after preparing the starch derivative is to heat an aqueous dispersion of the derivatized starch to gelatinize the derivatized starch. The gelatinization process disrupts, in whole or in part, the associative bonding of the starch molecule within the raw starch granule, thereby making the molecule more accessible to the enzyme and permitting the enzyme to more easily and uniformly debranch the starch molecules. After a slurry of the starch has been gelatinized, the solids, temperature and pH of the dispersion are adjusted to provide optimum enzyme activity.

The optimum parameters for enzyme activity will vary depending upon factors including enzyme concentration, substrate concentration, pH, temperature, the presence or absence of inhibitors and other factors. Depending on the type of enzyme, or its source, various parameters may require adjustment to achieve optimum debranching rate. In general, enzymatic debranching is carried out at the highest feasible solids content to facilitate subsequent drying of the starch while maintaining optimum debranching rates. For example, for the pullulanase used herein to produce a starch suitable for use in cosmetics, a precooked starch dispersion ranging up to 28% solids is preferred.

The practitioner will recognize that a higher solids starch system (e.g., above 50% solids) may be employed if the starch is gelatinized by a process which produces adequate mixing to uniformly blend the enzyme and the starch at higher solids. The practitioner also will recognize that the temperature, treatment time and other parameters of the enzymatic debranching process must be adjusted to the higher solids content. Processes which employ higher solids starch dispersions are intended to fall within the scope of this invention and may be used to prepare the short chain amylose.

Although the preparation of short chain amylose herein employs pullulanase (E.C. 3.2. 1.41; pullulan 6-glucanohydrolase) as the enzyme, other endo-alpha-1,6-glucanohydrolases, such as isoamylase (E.C. 3.2. 1.68), or any other endo-enzyme which exhibits selectivity in cleaving the 1,6-linkages of the starch molecule, leaving the 1,4-linkages substantially intact and releasing short chain amylose, may be used.

In a preferred embodiment, the enzyme used is a heat stable pullulanase obtained from a novel species of Bacillus. This pullulanase will catalyze the hydrolysis of the alpha-1,6 linkages in pullulan and amylopectin, provided that there are at least two glucose units in the side chain. Pullulanase is a linear polymer consisting essentially of D-glucopyranosyl triose units joined by alpha-1,6 linkages.

Optimum concentrations of enzyme and substrate are governed by the level of enzyme activity which will vary depending upon the enzyme source, the enzyme supplier and the concentration of the enzyme provided in commercially available batches. Although the process of this invention makes use of an enzyme in solution, processes utilizing an enzyme immobilized on a solid support are intended to fall within the scope of this invention.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3.0 to 7.5, with the preferred range being between 4.5 and 5.5, and the optimum being 5.0 when the temperature is 60° C. and the enzyme is the Bacillus pullulanase.

The aqueous starch dispersion should be held during the enzymatic debranching at a temperature of about 25°–100° C., the preferred range being 55°–65° C. and the optimum being 60° C. at pH 5.0 for the Bacillus pullulanase. However, if shorter treatment times are desired, a temperature range from 60°–65° C. or a higher enzyme concentration may be used. Alternatively, a higher temperature may be employed if a thermally stable debranching enzyme is selected for use herein. As with other parameters of the enzyme reaction, the preferred and optimum temperature ranges will vary with changes in other parameters such as substrate concentration, pH and other factors affecting enzyme activity, and can be determined by the practitioner.

The enzymatic treatment is permitted to continue until the desired amount of short chain amylose is produced. The progress of the enzymatic treatment may be measured by various methods. If all critical parameters have been established for achieving a particular starch composition, then the treatment may be allowed to proceed to a predetermined relative end point in time. The end point may be determined by change in viscosity of the starch dispersion, by gel permeation chromatography, by reducing group content, iodine reaction or by any other method known in the art for measuring the degree of enzymatic debranching of the starch molecule.

In a preferred embodiment, the debranching end point is measured by determining the viscosity of a starch dispersion at 72° F. (22° C.) using the funnel viscosity method set forth in Example 1, below. The funnel viscosity method is a rapid, simple method for determining viscosity, in which the amount of time needed for a standard quantity of starch slurry to flow through a standard size funnel is recorded.

In a second preferred embodiment, the degree of starch debranching is measured by gel permeation chromatography. After separating the starch into its different molecular weight fractions, the percentage of short chain amylose is determined by calculating the percentage, by weight, of the low molecular weight fraction of the partially debranched starch. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a percent low molecular weight fraction which may range up to 5% more or less than the percent short chain amylose of the starch sample.

The degree of starch debranching needed for a particular application depends on the type of starch utilized, the presence and nature of any substituent groups and the degree, if any, of conversion. The practitioner will be able to select a suitable starch and determine the necessary debranching for any particular cosmetic with a minimum of experimentation.

While any amylopectin-containing starch may be employed, the effects of enzymatic debranching will be more dramatic as the amylopectin content of the starch increases. Thus, although all commercially available starches may be employed herein, waxy maize which contains about 100% amylopectin is preferred.

In a preferred embodiment, waxy maize starch, or some other waxy starch (e.g., waxy rice or barley starch), is debranched, yielding sufficient short chain amylose to create a mixture comprising from 15 to 100% short chain amylose, and preferably, from 35 to 100% short chain amylose. This degree of debranching of waxy starches is preferred for creating a fat-like, lubricating texture in an aqueous starch dispersion. Fat-like properties are generally enhanced as the percent short chain amylose increases. Converted, debranched waxy starches (e.g., 50 WF acid-converted waxy maize or waxy rice) also are preferred for preparing a thermally reversible gel and providing lubricating qualities in an aqueous starch dispersion.

For preparing high strength starch gels, partially debranched corn starch, comprising 10 to 45% short chain amylose, and preferably 15 to 40% short chain amylose, is preferred.

After the desired degree of starch debranching has been reached, the enzyme may be deactivated. Pullulanase is rapidly deactivated at temperatures above about 70° C., therefore, the reaction may be conveniently terminated by increasing the temperature of the starch dispersion to at least 75° C. for about 15 minutes.

If use in cosmetics requires purification of the debranched starch, the reaction impurities and by-products may be removed by dialysis, filtration, ion exchange processes, centrifugation or any other method known in the art for isolating and recovering the starch.

If a dried starch is desired for cosmetics applications, the starch may be dehydrated by any method known in the art.

It is to be understood that the invention includes starch blends which contain 15 to 100% short chain amylose. Thus, this invention includes blends of debranched starch and other components, such as chemically modified starches and other polymers, and includes multi-step processes in which an enzyme is employed in one step to debranch starch. For example, this invention includes multi-step processes and starch blends wherein the starch is converted, derivatized, crosslinked or otherwise modified in addition to being subjected to enzymatic debranching, or being blended with short chain amylose.

The debranched starch may be employed alone, or as a starch blend, in any cosmetic formulation. The nature of the cosmetic formulation will direct the selection of an appropriate debranched starch from those disclosed herein. In a preferred embodiment, a cosmetic stick formulation comprises 1 to 16% starch which has been enzymatically debranched to yield from 15 to 100%, by weight, short chain amylose; 2 to 35% water; 35 to 90% hydrophobic base, selected from the group consisting of oil, wax and fat; 5 to 20% emulsifier(s); and one or more adjuncts selected from dye(s), preservative(s), fragrance(s), flavor(s), sunscreen agent(s), opacifier(s), and filler(s).

In another preferred embodiment enzymatically debranched starch is employed in a cosmetic composition disclosed in U.S. Pat. No. 4,970,220, to Chaussee, issued Nov. 13, 1990, which is hereby incorporated by reference.

The following examples will more fully illustrate the embodiments of this invention. In these examples, all parts and percentages are given by dry weight basis and all temperature are in degrees Celsius unless otherwise noted.

EXAMPLE 1

This example illustrates the preparation of representative partially debranched starches by the process of this invention.

The starches were converted, derivatized or crosslinked, where applicable, prior to gelatinization and treatment with pullulanase. To convert the starch, a slurry of 100 parts of starch in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

STARCH DERIVATIZATION

To prepare the octenylsuccinate derivative, 100 parts of starch was slurried in 150 parts water, the pH was adjusted to 7.5 with sodium hydroxide, and the indicated amount of octenylsuccinic anhydride was added slowly while the pH was maintained at 7.5 with alkali. The reaction was complete when no further addition of alkali was necessary. The pH was adjusted to between 4.0 and 6.5 and the resulting derivatives were recovered by filtration, washed and dried.

To prepare the acetate derivative, 100 parts of the starch was slurried in 150 parts by water, adjusting the pH to 8.3 with 3% sodium hydroxide solution, and slowly adding the indicated amount of acetic anhydride while maintaining the pH at 8.3 with the above alkali. The reaction was complete when no further addition of alkali was necessary. The pH was adjusted to between 4.0 and 6.5 and the resulting derivative was recovered as above.

The crosslinked starch was prepared by slurrying 100 parts of starch in 150 parts water, adding 0.8 parts sodium hydroxide, 1.0 parts sodium chloride, and then adding the indicated amount of phosphorus oxychloride. The slurry was agitated for 3 hours at room temperature. When the reaction was completed, the pH was adjusted to 5.5 with acid. The starch was recovered by filtration, washed and dried.

STARCH DEBRANCHING

An aqueous slurry (20–30% solids) was prepared employing the desired starch. The aqueous starch slurry was jet-cooked at approximately 300° F. (149° C.) to gelatinize the starch. The cooked starch dispersion was placed in a constant temperature bath at 58°–60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucano-hydrolase) which was used is produced by a novel species of Bacillus. This enzyme (Promozyme®) was obtained from Novo Industri A/S of Denmark. The enzymatic activity of Promozyme in a 1.25 g/ml solution is standardized at 200 PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S.

Thus, in the starch dispersion employing corn starch, 125 PUN of pullulanase per 100 g corn starch was added to the dispersion. For the waxy maize starch slurry (with higher amylopectin content), 750 PUN of pullulanase per 100 g waxy maize starch was added to the dispersion.

The amount of debranching was measured initially by the funnel viscosity test and subsequently by gel permeation chromatography.

FUNNEL VISCOSITY MEASUREMENT

To measure funnel viscosity at 19% solids, 38 g of the starch (anhydrous basis) was weighed into a tared 250 ml beaker (stainless steel) containing a thermometer and brought to 200 g total weight with distilled water. The sample was mixed to dissolve any lumps and heated or cooled to 72° F. (22° C.). A total of 100 ml of the cooked starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml samples to flow through the apex of the funnel was recorded.

The funnel was a standard 58°, thick-wall, resistance glass funnel whose top diameter was about 9–10 cm with the inside diameter of the stem being about 0.381 cm. The funnel was calibrated so as to allow 100 ml of water to go through in 6 seconds using the above procedure.

CORN STARCH (CAUSTIC) FUNNEL VISCOSITY

Due to retrogradation of the starch which occurs when using corn starch, the funnel viscosity measurement was modified as follows for debranched corn starch:

1. the starch sample weight was reduced to 15 g (anhydrous basis);
2. sufficient hot (at least 90° C.) water was added to the starch to bring it to 150 g total weight;
3. 15 g of 25% w/v sodium hydroxide solution was added to the hot starch slurry; and
4. with stirring, the slurry was cooled to 72° F. (22° C.) and the measurement carried out as set forth above.

GEL PERMEATION CHROMATOGRAPHY

Starches were prepared for analysis by slurrying 5 mg of starch in 4 ml of dimethylsulfoxide ("DMSO") containing 0.03M sodium nitrate and heating the slurry to 80° C. for at least 30 minutes to dissolve the starch. Samples (200 μl) were injected into an ALC/GPC-150C Chromatograph (Waters Associates, Milford, Mass.) (equipped with a Nelson 3000 Series Chromatography Data System and two PL gel mixed 10 μm columns (obtained from Polymer Laboratory, Amherst, Mass.), employing DMSO containing 0.03M sodium nitrate as the mobile phase) and eluted at a rate of 1 ml/min. The columns were calibrated using dextran standards (with molecular weights of 2,000; 20,000; 80,000; 500,000; and 2,000,000 obtained from Pharmacia Fine Chemicals, Piscataway, N.J.). The percentage short chain amylose was calculated from the relative area of the peak obtained within the molecular weight range from 500 to 20,000.

PREPARATION OF DEBRANCHED OSA WAXY MAIZE STARCHES

Employing the process set forth above, an OSA starch derivative was prepared by reacting 4,000 g of waxy maize starch with 1% octenylsuccinic anhydride. The starch was then jet cooked at pH 5.0 yield a 23% starch dispersion. Pullulanase (80 mls) was added to the dispersion at 58° C. with agitation. After 24, hours, the funnel viscosity was 35 seconds at 19% solids and 72° F. (22° C.).

The debranching was continued by adding an additional 80 mls of pullulanase at 58° C. and agitating the dispersion for an additional 3 hours. The pullulanase was deactivated by heating the dispersion to about 80° C. The funnel viscosity was 12 seconds at 19% solids and 72° F. (22° C.). The starch dispersion was spray dried at an inlet temperature of 200°–210° C. and an outlet temperature of 80°–90° C. The spray-dried starch was screened through #40 mesh screen.

A second sample of OSA waxy maize starch (4,000 g) was prepared and debranched in the same manner as the first sample, except that 20 mls of pullulanase was employed in a single addition. Debranching continued for two hours at which time the funnel viscosity was 50 seconds at 10% solids and 72° F. (220° C.). This sample was spray-dried in the same manner as the first sample.

EXAMPLE 2

This example illustrates the preparation of partially debranched starch employing the enzyme isoamylase (glycogen 6-glucano-hydrolase; E.C. 3.2.1.68).

A cooked, 24% solids, aqueous dispersion of waxy maize starch (2,500 g) was treated with 5,000 units of a *Pseudomonas amyloderamosa* isoamylase (obtained from Sigma Chemical Company, St. Louis, Mo.). One unit of this isoamylase causes an increase in absorbance ($A_{610}$) of 0.1 in 1 hour using rice starch as a substrate.

The starch dispersion was heated to 45° C. at pH 4.0, the enzyme was added and the mixture was stirred for 26 hours. A portion of the mixture was removed, heated to 80° C. to deactivate the enzyme, and spray-dried and screened as in Example 1. The remaining portion of the starch mixture was enzymatically treated for a total of 43 hours, at which time the enzyme was deactivated and the starch dried and screened as above.

The quantity of short chain amylose obtained from isoamylase hydrolysis was measured with gel permeation chromatography. The 26 hour sample contained 21.9% and the 43 hour sample contained 28.4% short chain amylose.

EXAMPLE 3

This example illustrates the relationships between treatment time, funnel viscosity (or Water Fluidity) and percentage short chain amylose of the starches of this invention.

The partial enzymatic debranching process of Example 1 was carried out on the starches listed in Table I.

The funnel viscosity and percent short chain amylose were measured by the methods as set forth above. Results are shown in Table I.

TABLE I

| Starch | Treatment Time (hrs.) | Funnel Viscosity (seconds) | % Solids | % Short Chain Amylose |
|---|---|---|---|---|
| Waxy-Maize Acid-converted to 50 WF | | | | |
| 1 | 0.5 | 110 | 19 | 13.5 |
| 2 | 1.0 | 22 | 19 | 26.3 |
| 3 | 20.0 | 20 | 19 | 27.1 |
| 4 | 20.0 | 18 | 19 | 31.8 |
| 5 | 25.0 | 14 | 19 | 35.1 |
| 6 | 44.0 | 12 | 19 | 48.0 |
| Waxy-Maize | | | | |
| 1 | 0.25 | 110 | 19 | 22.1 |
| 2 | 1.0 | 52 | 19 | 23.8 |
| 3 | 20.0 | 20 | 19 | 32.6 |
| 4 | 20.0 | 16 | 19 | 40.0 |
| 5 | 24.0 | 12 | 19 | 45.6 |
| 6 | 45.0 | 12 | 19 | 51.9 |
| Corn[a] | | | | |
| 1 | 1.0 | 97 | 10 | 14.5 |
| 2 | 3.0 | 37 | 10 | 21.9 |
| 3 | 5.0 | 30 | 10 | 26.5 |
| 4 | 7.0 | 27 | 10 | 24.9 |
| 5 | 24.0 | 18 | 10 | 33.3 |
| 6 | 48.0 | 12 | 10 | 47.5 |

[a]Caustic Funnel Viscosity.

The results show generally that as reaction time increases, the percent short chain amylose increases and the funnel viscosity decreases in a non-linear fashion. Thus, one or more of these measurements may be employed to measure the progress of the enzymatic debranching.

EXAMPLE 4

This example illustrates that the starch of this invention may be used to create lubricity and fat-like texture in an aqueous starch dispersion.

A waxy maize starch was partially debranched by the method of Example 1 to a funnel viscosity of 10–12 seconds at 72° F. (22° C.) and 10% solids (about 50% short chain amylose).

Fat-like or lubricating properties of the starch were evaluated by dispersing 25 g, anhydrous, of starch in 75 g of distilled water. The dispersion was heated on a steam bath for 20 minutes, poured into a petri dish, refrigerated for one hour and subjectively evaluated. The partially debranched starch gel was spread on the palm of the hand and observed to have a lubricating, creamy touch. The gel was glossy and opaque.

Additional starches and starch blends were tested by the same method for fat-like properties in aqueous dispersions. These starches and starch blends and the test results are set forth in Table II, below. All samples exhibited fat-like properties, including blends of debranched waxy maize with tapioca maltodextrin or converted waxy maize or converted tapioca. The short chain amylose content of the debranched waxy maize starch ranged from 15 to 75%, by weight.

TABLE II

CHARACTERISTICS OF AQUEOUS DISPERSIONS OF DEBRANCHED STARCHES

| Percent of Starch in Blend | | | | | | |
|---|---|---|---|---|---|---|
| Debranched Starch | | | | Converted Starch[e] | | |
| Waxy Maize | | | Tapioca | 35WF | 81WF | Evaluation in Aqueous Dispersion |
| A[a] | B[b] | C[c] | Maltodextrin[d] | Waxy Maize | Tapioca | (25% solids dispersion) |
| 100 | — | — | — | — | — | glossy, opaque, creamy gel, spreadable |
| 80 | — | — | 20 | — | — | opaque, creamy, shortening |
| 60 | — | — | 40 | — | — | opaque, butter-like. |
| 20 | — | — | 80 | — | — | opaque, oily |
| 50 | — | — | — | — | 50 | opaque, creamy, spreadable |
| 75 | — | — | — | — | 25 | opaque, creamy, spreadable |
| — | 100 | — | — | — | — | creamy, greasy, slight tack |
| — | 50 | — | — | — | 50 | creamy, buttery |
| — | — | 100 | — | — | — | creamy, spreadable gel |
| — | — | 50 | — | 50 | — | creamy, soft, greasy, spreadable gel |

[a]50% short chain amylose
[b]15% short chain amylose
[c]>75% short chain amylose
[d]an alpha-amylose converted, pregelatinized tapioca starch of the type disclosed in U.S. Pat. No. 4,510,166 to Lechin, et al.
[e]an acid-converted starch, converted by the method of Example 1.

EXAMPLE 5

This example illustrated the preparation of a lipstick formulation using an aqueous dispersion of enzymatically debranched starch.

Lipsticks were prepared using the following formulation and procedure.

LIPSTICK FORMULATION

| INGREDIENT | PERCENT BY WEIGHT |
|---|---|
| Phase A | |
| Starch[a] | 10.00 |
| Distilled Water | 30.00 |
| Phase B | |
| Castor Oil | 30.00 |
| Candelilla Wax | 15.00 |
| Isopropyl Myristate | 7.00 |
| Sorbitan oleate | 1.00 |
| Polysorbate 80 | 3.00 |
| Dimethicone | 3.00 |
| Phase C | |
| Preservative[b] | 1.00 |
| | 100.00 |

[a]See Table III, below.
[b]A mixture of propylene glycol, diazolidinyl urea, methylparaben and propylparaben.

Starches were prepared by the method of Example 1. The starch was slowly sifted into the water with agitation, heated to 80° C. and held for 30 minutes. The components of phase B were combined and heated to 80° C. with mixing. When both phases were completely dispersed, phase B was added to phase A with mixing and held at 80° C. for 30 minutes. This formulation was cooled to 40° C. with mixing and phase C was added.

Using this procedures, a series of lipstick samples were prepared from the debranched starches and control starches set forth in Table III, below. The samples were evaluated for the following tactile and visual properties:

Soft feel to the lips,

Good spreading properties,

Smooth texture, and

Rigid stick form.

The lipsticks were subjected to elevated temperature studies to simulate accelerated shelf life. Formulations were prepared and sealed in glass jars. Samples were placed in a closed oven at 49° C. (120° F.) and examined periodically, Results of the quality evaluations and the storage tests are set forth in Table III.

TABLE III

| Starch Sample[a] | Lipstick Quality | Lipstick Stability |
|---|---|---|
| Control | phase separation | phase separation |
| Debranched converted waxy maize (58%)[c] | smooth | stable |
| Debranched 1% OSA waxy maize (47%)[c] | smooth | stable |
| Debranched 3% quab 342 waxy maize (30%)[c] | smooth | stable |
| Debranched 3% quab 426 waxy maize (30%)[c] | smooth | stable |
| α-amylase converted 3% OSA waxy maize | smooth | phase separation |

TABLE III-continued

| Starch Sample[a] | Lipstick Quality | Lipstick Stability |
|---|---|---|
| α-amylase converted 1% OSA waxy maize | smooth | phase separation |
| 3% OSA waxy maize | grainy texture | stable |
| Tapioca dextrin | grainy texture | stable |
| α-amylase converted waxy maize (pregelatinized) | smooth | phase separation |
| Corn starch | b | b |
| Crosslinked, pregelatinized tapioca | b | b |
| Acid-converted high amylose (50%) corn | b | b |
| 10% quab 342 corn (contains 0.4% Nitrogen) | b | b |
| Corn dextrin | grainy texture | phase separation |
| Acid-converted corn | smooth | phase separation |

[a]OSA is Octenyl succinic Anhydride derivative of the starch; Quab 342 is a 3 Chloro-2-Hydroxypropyl-N,N,N-Dimethyldodecyl Ammonium Chloride derivative of the starch; Quab 426 is a 3-Chloro-2-Hydroxypropyl-N,N,N-dimethyloctydectyl Ammonium Chloride derivative of the starch; and phosphorous oxychloride was used for crosslinking. All starch derivatizations and conversions were by the methods set forth in Example 1.
[b]These starches could not be prepared in the suggested formulation at 10% due to the high viscosity of the aqueous phase. The starch were incorporated at 5% and all but the acid-converted high amylose (50%) corn starch could not be prepared. The acid-converted high amylose (50%) corn starch provided a smooth feeling formulation which phase Separated after two weeks at 49° C. (120° F.).
[c]Percent short chain amylose.

Only the pullulanase debranched starches produced stable formulations with desirable features. After two months, debranched starch-containing formulations showed no signs of instability, i.e., perspiration like droplets or liquid separation, indicating phase separation. Also, no signs of cracking or discoloration occurred.

Thus, the utility of starch in water-in-oil stick cosmetic compositions was limited to the debranched starches herein. Other modified and unmodified starches were not acceptable in these cosmetics.

EXAMPLE 6

This example illustrates the preparation of various skin lotions using enzymatically debranched starch.

Skin lotions were prepared according to the following formulations and procedures.

| HAND AND BODY LOTION FORMULATION | |
|---|---|
| INGREDIENTS | PERCENT BY WEIGHT |
| Phase A | |
| Cetyl Alcohol | 1.00 |
| 20 mole Ethoxy Stearyl Alcohol | 1.00 |
| Glyceryl Stearate SE | 1.00 |
| $C_{12}$–$C_{15}$ Alcohols Benzoate | 3.00 |
| Octyl Palmatate | 3.00 |
| Stearic Acid | 2.00 |
| Dimethicone Copolyol | 1.00 |
| Phase B | |
| Deionized Water | 69.00 |
| Propylene Glycol | 3.00 |
| Fully Debranched Potato Starch[a] | 2.00 |
| Carbomer 941 (2% Solution) | 12.00 |
| Triethanolamine (99%) | 1.00 |
| Phase C | |
| Preservative[b] | 1.00 |
| | 100.00 |

| HAND AND BODY LOTION FORMULATION | |
|---|---|
| INGREDIENTS | PERCENT BY WEIGHT |

[a]Starch contained 89.2% short chain amylose and was prepared by the method of Example 1.
[b]A mixture of propylene glycol, diazolidinyl urea, methylparaben and propylparaben.

The ingredients in Phase B were mixed and heated to 80° C. The ingredients in phase A were mixed, heated to 80° C. and added to Phase B. The formulation was mixed for 15 minutes at 80° C., allowed to cool to 35° C. and Phase C was added. The formulation was cooled to room temperature and packaged.

The formulation was very white, creamy and viscous but difficult to rub into the skin (i.e., a large amount of drag on the skin). The formulation was unacceptable as a hand lotion. The formulation had tactile properties typical of a night cream.

| CATIONIC SKIN MOISTURIZER FORMULATION (MULTI-PROTECTION) | |
|---|---|
| Ingredients | Percent by Weight |
| Phase A | |
| Cetyl Alcohol | 2.00 |
| Mineral oil | 3.00 |
| Petrolatum | 1.00 |
| Tridecyl Neopentanoate | 2.50 |
| Dimethicone copolyol | 1.00 |
| Glyceryl Stearate and Laureth-23 | 1.00 |
| Dimethicone | 0.20 |
| Tocopheryl Acetate | 0.20 |
| Steareth-21 | 1.00 |
| Phase B | |
| Deionized Water | 70.90 |
| Stearamidopropyl PG-Dimonium Chloride Phosphate (Monaquat) | 2.00 |
| Allantonin | 0.50 |

-continued

CATIONIC SKIN MOISTURIZER FORMULATION (MULTI-PROTECTION)

| Ingredients | Percent by Weight |
|---|---|
| Aloe Vera Gel (1:1) | 5.00 |
| Polyquaternium-10 (Celquatg SC-240) | 0.50 |
| Propylene Glycol | 4.00 |
| Debranched 1% OSA waxy maize starch[a] | 4.00 |
| Phase C | |
| Preservative[b] | 1.00 |
| Phase D | |
| Fragrance Q4698 | 0.20 |
| | 100.00 |

[a]Debranched by the method of Example 1 to 74.7% short chain amylose.
[b]A mixture of propylene glycol, diazolidinyl urea, methylparaben and propylparaben.

The water, monaquat and allatonin were heated to 50°. Celquat SC-240 was dispersed thoroughly in the water and heated to 80° C. The propylene glycol and starch were slurried and added to the water phase. Phase B was mixed and heated to 80° C., Phase A was added to Phase B at 80° C., and mixed for 15 minutes at 80° C., cooled to 35° C. and Phase C and Phase D were added. The formulation was cooled to room temperature and packaged.

The formulation initially left a wet feeling on the skin but dried to a silky residue. The formulation was white and creamy and acceptable when used on the skin.

EMOLLIENT LOTION FORMULATION

| Ingredients | Percent by Weight |
|---|---|
| Phase A | |
| Cetyl Alcohol | 1.00 |
| Ceteth-20 | 1.00 |
| Glyceryl Stearate SE | 1.00 |
| $C_{12-15}$ Alcohols Benzoate | 5.00 |
| Octyl Palmitate | 5.00 |
| Stearic Acid T.P. | 2.00 |
| Dimethicone Copolyol | 1.00 |
| Phase B | |
| Deionized water | 77.31 |
| Carbomer 941 | 0.24 |
| Triethanolamine (99%) | 1.00 |
| Propylene Glycol | 3.00 |
| Debranched waxy maize starch[a] | 2.00 |
| Methylparaben | 0.15 |
| Propylparaben | 0.10 |
| Phase C | |
| Diazolidinyl Urea | 0.20 |
| | 100.00 |

[a]Debranched by the method of Example 1 to 12.2% short chain amylose.

The carbopol was dispersed into the water and heated to 80° C. The remaining Phase B ingredients were added and mixed thoroughly. Phase A was mixed, heated to 80° C. and added to Phase B. The formulation was mixed for 15 minutes at 80° C., cooled to 40° C. and Phase C was added. The formulation was cooled to room temperature and packaged.

The formulation was non-greasy, non-tacky and acceptable when used on the skin.

EXAMPLE 7

This example illustrates the preparation of various emulsion-containing cosmetic compositions using enzymatically debranched starch.

Cosmetic compositions are prepared according to the following formulations and procedures.

NON-GREASY LOTION FORMULATION

| Ingredient | Percent by Weight |
|---|---|
| Phase A | |
| Cetyl Alcohol | 1.00 |
| Glyceryl Stearate | 1.00 |
| Ceteth-20 | 1.00 |
| Octyl Palmitate | 3.00 |
| Dimethicone Copolyol | 1.00 |
| Stearic Acid T.P. | 3.00 |
| Phase B | |
| Deionized Water | 86.35 |
| Carbomer 941 | 0.20 |
| Triethanolamine (99%) | 1.00 |
| Debranched Waxy Maize Starch[a] | 2.00 |
| Methylparaben | 0.15 |
| Propylparaben | 0.10 |
| Phase C | |
| Diazolidinyl Urea | 0.20 |
| | 100.00 |

[a]Debranched by the method of Example 1 to 78% short chain amylose.

Preparation of the non-greasy lotion is by the method set forth in Example 6 for the emollient lotion.

DRY SKIN LOTION FORMULATION

| Ingredients | Percent by Weight |
|---|---|
| Phase A | |
| Cetyl Alcohol | 1.00 |
| Ceteth-21 | 1.00 |
| Glyceryl Stearate SE | 1.00 |
| Tridecyl Neopentanoate | 5.00 |
| Octyl Palmitate | 3.00 |
| Stearic Acid T.P. | 2.00 |
| Dimethicone | 0.50 |
| Phase B | |
| Deionized water | 79.80 |
| Carbomer 941 | 0.25 |
| Triethanolamine (99%) | 1.00 |
| Propylene Glycol | 3.00 |
| Debranched waxy maize starch[a] | 2.00 |
| Methylparaben | 0.15 |
| Propylparaben | 0.10 |
| Phase C | |
| Diazolidinyl urea | 0.20 |
| | 100.00 |

[a]Debranched by the method of Example 1 to 78% short chain amylose.

The dry skin lotion is prepared by the same method as the non-greasy lotion.

BABY LOTION FORMULATION

| Ingredients | Percent by Weight |
| --- | --- |
| Phase A | |
| $C_{12-15}$ Alcohols Benzoate | 10.00 |
| Stearic Acid T.P. | 2.50 |
| Glyceryl Stearate SE | 2.00 |
| Ceteth-20 | 1.00 |
| Tocopheryl Acetate | 0.50 |
| Cetyl Alcohol | 1.00 |
| Dimethicone Copolyol | 1.00 |
| Phase B | |
| Deionized water | 68.15 |
| Carbomer 934 | 0.20 |
| Triethanolamine (99%) | 1.20 |
| Aloe vera gel (1:1) | 10.00 |
| Debranched waxy maize starch[a] | 2.00 |
| Methylparaben | 0.15 |
| Propylparaben | 0.10 |
| Phase C | |
| Imidazolidinyl Urea | 0.20 |
| | 100.00 |

[a]Debranched by the method of Example 1 to 78% short chain amylose.

The baby lotion is prepared by the same method as the non-greasy lotion.

MOISTURIZER SUNSCREEN FORMULATION (EVERYDAY; S.P.F. 6)

| Ingredients | Percent by Weight |
| --- | --- |
| Phase A | |
| Octyl Salicylate | 3.00 |
| Benzophenone-3 | 2.00 |
| $C_{12-15}$ alcohols benzoate | 5.00 |
| Stearic Acid T.P. | 2.00 |
| Glyceryl Stearate SE | 2.00 |
| Tocopheryl Acetate | 0.20 |
| Cetyl Alcohol | 1.00 |
| PEG-40 Stearate | 1.00 |
| Dimethicone Copolyol | 1.00 |
| Phase B | |
| Deionized water | 72.00 |
| Carbomer 941 | 0.15 |
| Triethanolamine (99%) | 0.70 |
| Aloe Vera Gel (1:1) | 5.00 |
| Glycerin | 3.00 |
| Methylparaben | 0.15 |
| Propylparaben | 0.10 |
| Debranched OSA waxy maize starch[a] | 1.50 |
| Phase C | |
| Diazolidinyl Urea | 0.20 |
| | 100.00 |

[a]Debranched by the method of Example 1 to 78% short chain amylose and treated with 3% OSA treated.

The moisturizer sunscreen formulation is prepared by the same method as the non-greasy lotion.

FACIAL MASK FORMULATION

| Ingredients | Percent by Weight |
| --- | --- |
| Phase A | |
| Deionized water | 87.55 |
| Carbomer 934 | 0.50 |
| Triethanolamine (99%) | 0.50 |
| Polysorbate 80 | 1.00 |
| Debranched waxy maize starch[a] | 10.00 |
| Methylparaben | 0.15 |
| Propylparaben | 0.10 |
| Phase B | |
| Diazolidinyl Urea | 0.20 |
| | 100.00 |

[a]Debranched by the method of Example 1 to 60% short chain amylose.

The facial mask formulation is prepared by the same method as the non-greasy lotion, except that no Phase C is used.

CLEANSING CREAM FORMULATION

| Ingredients | Percent by Weight |
| --- | --- |
| Phase A | |
| Stearic Acid D.P. | 20.00 |
| Mineral Oil | 5.00 |
| Cetyl Alcohol | 0.50 |
| octyl Palmitate | 5.00 |
| Phase B | |
| Deionized water | 61.05 |
| Propylene Glycol | 5.00 |
| Debranched waxy maize starch[a] | 2.00 |
| Triethanolamine (99%) | 1.00 |
| Methylparaben | 0.15 |
| Propylparaben | 0.10 |
| Phase C | |
| Imidazolidinyl Urea | 0.20 |
| | 100.00 |

[a]Debranched by the method of Example 1 to 31.7% short chain amylose.

p The cleansing cream formulation is prepared by the same method as the non-greasy lotion.

OIL-FREE EMOLLIENT LOTION FORMULATION

| Ingredients | Percent by Weight |
| --- | --- |
| Phase B | |
| Fully debranched waxy maize[a] | 25.0 |
| Propylene glycol | 0.5 |
| Polysorbate 20 | 1.0 |
| Dimethicone copolyol | 2.0 |
| Deionized water | 70.0 |
| Phase C | |
| Preservative[b] | 1.5 |
| | 100.00 |

[a]Debranched by the method of Example 1 to 78% short chain amylose.
[b]A mixture of propylene glycol, diazolidinyl urea, methylparaben and propylparaben.

The oil-free formulation is prepared by the same method as the non-greasy lotion, except that no Phase A is used. The oil-free, emulsion-like lotion is opaque and viscous. It may be used as a carrier or base for pharmacologically active agents.

Various modifications and improvements on the compositions herein will become readily apparent to those skilled in the art. Accordingly, the scope and spirit of the invention are to be limited only by the claims and not by the foregoing specification.

We claim:

1. An improved water-in-oil emulsion- or oil-free emulsion-containing skin cosmetic lotion, wherein the improvement comprises an effective amount of an aqueous dispersion of 15–40% solids, by weight, of a procooked, cold-water-swelling waxy starch which is enzymatically debranched by treatment with an alpha-1,6-D-glucanohydrolase to yield 35% to 100%, by weight, short chain amylose and which is present in an amount sufficient to create a fat-like lubricating texture in the aqueous starch dispersion.

2. The lotion of claim 1, wherein the waxy starch is selected from the group consisting of waxy maize, waxy rice, and waxy barley.

3. The lotion of claim 2, wherein the waxy starch is waxy maize debranched to yield a mixture containing from 75 to 78% short chain amylose.

4. The lotion of claim 1, wherein the waxy starch is a waxy maize derivatized with octenylsuccinic acid.

5. The lotion of claim 1, wherein the waxy starch is a waxy maize derivatized with 3-chloro-2-hydroxypropyl-N,N,N-dimethyldodecyl ammonium chloride or 3-chloro-2-hydroxypropyl-N,N,N-dimethyloctyldecyl ammonium chloride acid.

6. The lotion of claim 1, wherein the aqueous dispersion further consists essentially of a pregelatinized tapioca maltodextrin or converted tapioca starch having a water fluidity of 81.

7. The lotion of claim 1, wherein the lotion is a skin lotion.

8. The oil-free cosmetic composition of claim 1, further comprising 0.5 to 15% emulsifier(s); 0.5–5% preservative(s); and one or more adjuncts selected from the group consisting of dye(s); fragrance(s); flavor(s); filler(s); and opacifier(s).

9. The lotion of claim 1, wherein the debranched waxy starch is an acid-converted maize or waxy rice having a water fluidity of 50.

10. The improved cosmetic skin lotion of claim 1, wherein the lotion is the water-in-oil emulsion-containing lotion.

11. The improved cosmetic skin lotion of claim 1, wherein the lotion is the oil-free emulsion-containing lotion.

12. The lotion of claim 7 wherein the lotion is selected from the group consisting of a moisturizing lotion, an emollient lotion, and a baby lotion and wherein the amount of the starch is 1.5–25% by weight of the total lotion.

* * * * *